United States Patent
Oguri et al.

(10) Patent No.: US 9,435,772 B2
(45) Date of Patent: Sep. 6, 2016

(54) HEATING APPARATUS FOR A GAS CHROMATOGRAPH, AND HEATING METHOD FOR A GAS CHROMATOGRAPH

(71) Applicant: Japan Analytical Industry Co., Ltd., Nishitama-gun, Tokyo (JP)

(72) Inventors: Naoki Oguri, Nishitama-gun (JP); Kaoru Enokido, Nishitama-gun (JP)

(73) Assignee: Japan Analytical Industry Co., Ltd., Tokyo (JP)

( * ) Notice: Subject to any disclaimer, the term of this patent is extended or adjusted under 35 U.S.C. 154(b) by 247 days.

(21) Appl. No.: 14/344,495

(22) PCT Filed: May 2, 2013

(86) PCT No.: PCT/JP2013/063228
§ 371 (c)(1),
(2) Date: Mar. 12, 2014

(87) PCT Pub. No.: WO2014/178147
PCT Pub. Date: Nov. 6, 2014

(65) Prior Publication Data
US 2015/0125962 A1    May 7, 2015

(51) Int. Cl.
*G01N 31/12* (2006.01)
*G01N 30/24* (2006.01)
(Continued)

(52) U.S. Cl.
CPC .............. *G01N 30/12* (2013.01); *G01N 30/06* (2013.01); *G01N 30/20* (2013.01); *G01N 2030/125* (2013.01)

(58) Field of Classification Search
CPC .............................. G01N 31/12; G01N 30/24

USPC ............ 422/78, 80, 540; 436/145, 155, 436/157–158, 161
See application file for complete search history.

(56) References Cited

U.S. PATENT DOCUMENTS 3,560,160 A * 2/1971 Lanneau ................ G01N 27/16
422/51
3,684,454 A * 8/1972 Martin ................... G01N 27/16
219/499
(Continued)

FOREIGN PATENT DOCUMENTS

JP          61-204561      *   9/1986
JP          1-203970       *   8/1989
(Continued)

OTHER PUBLICATIONS

Oguri, N. et al, Journal of High Resolution Chromatography 1992, 15, 9-12.*
(Continued)

*Primary Examiner* — Arlen Soderquist
(74) *Attorney, Agent, or Firm* — Sughrue Mion, PLLC

(57) ABSTRACT

To provide a heating apparatus for a gas chromatograph, and a heating method for a gas chromatograph, wherein vapor phase components can be analyzed at an arbitrary temperature and can be instantaneously heated and pyrolized at a set temperature, thereby enabling analysis to be carried out with good reproducibility. The heating apparatus for a gas chromatograph 10 is structured in that the ceramic heater 33 is disposed around the periphery of the sample tube 31 to heat the sample 1 housed in the sample tube 31, the temperature of the sample 1 is incrementally elevated, and the high-frequency coil 35, disposed around the periphery of the ceramic heater 33, heats the pyrofoil 32 wrapping the sample 1 to the Curie point, and the sample 1 is instantaneously heated and pyrolized.

8 Claims, 3 Drawing Sheets

(51) Int. Cl.
*G01N 30/12* (2006.01)
*G01N 30/06* (2006.01)
*G01N 30/20* (2006.01)

(56) References Cited

U.S. PATENT DOCUMENTS

| | | | | |
|---|---|---|---|---|
| 3,703,355 A | * | 11/1972 | Takahashi | G01N 31/12 422/78 |
| 3,879,181 A | * | 4/1975 | Nakamura | G01N 30/12 96/104 |
| 4,159,894 A | * | 7/1979 | Hu | G01N 30/12 422/78 |
| 4,408,125 A | * | 10/1983 | Meuzelaar | H01J 49/04 250/288 |
| 4,980,131 A | * | 12/1990 | Meuzelaar | G01N 31/12 422/78 |
| 5,049,509 A | * | 9/1991 | Szakasits | G01N 30/40 422/89 |
| 6,453,725 B1 | * | 9/2002 | Dahlgren | F16K 11/022 137/863 |
| 2004/0149011 A1 | * | 8/2004 | Staphanos | G01N 30/30 73/23.42 |

FOREIGN PATENT DOCUMENTS

| | | |
|---|---|---|
| JP | 2-9864 U | 1/1990 |
| JP | 4-318457 * | 11/1992 |
| JP | 6-180306 * | 6/1994 |
| JP | 8-5620 * | 1/1996 |
| JP | 3965234 B2 | 8/2007 |
| JP | 2013-011452 A | 1/2013 |

OTHER PUBLICATIONS

Onishi, A. et al, Journal of High Resolution Chromatography 1993, 16, 353-357.*

Jeon, S. J. et al, Journal of Air & Waste Management 2001, 51, 766-784.*

Buco, S. et al, Journal of Chromatography A 2004, 1026, 223-229.*

* cited by examiner

HEATING APPARATUS FOR A GAS CHROMATOGRAPH, AND HEATING METHOD FOR A GAS CHROMATOGRAPH

CROSS REFERENCE TO RELATED APPLICATION

This application is a National Stage of International Application No. PCT/JP2013/063228 filed May 2, 2013, the contents of which are incorporated herein by reference in their entirety.

TECHNICAL FIELD

The present invention relates to a heating apparatus for a gas chromatograph for analyzing a low molecular or a high molecular material or the like as a sample when a gas chromatograph is used, and to a heating method for a gas chromatograph.

BACKGROUND ART

Patent reference 1 describes a thermal analysis apparatus used as a conventional heating apparatus for a gas chromatograph. In this thermal analysis apparatus, a sample is placed in a pyrolysis furnace in which a heater is used to elevate the temperature, and vapor phase components produced by heating the sample are analyzed. With this thermal analysis apparatus, when the pyrolysis furnace is heated by the heater, the vapor phase components are produced from volatile components of the heated sample. When the temperature of the pyrolysis furnace is further elevated, high molecular components of the sample are pyrolized to low molecular components, thereby producing mixed vapor phase components. As the sample is thus heated up incrementally, a heart-cut can be used to analyze gas phase components at an arbitrary temperature.

PRIOR ART REFERENCES

Patent Reference

Patent reference 1: Japanese Patent No. 3965234

SUMMARY OF THE INVENTION

Problem to be Solved by the Invention

However, in the above-described conventional thermal analysis apparatus when the heater is used to heat up the pyrolysis furnace the sample is heated incrementally, for example, the temperature is raised in increments of 20° C. per minute, so that reproducibility is worse.

The present invention is proposed in the light of the above situation. Namely, an object of the present invention is to provide a heating apparatus for a gas chromatograph, and a heating method for a gas chromatograph, that enables vapor phase components to be analyzed at an arbitrary temperature, and can instantaneously heat at a set temperature to pyrolyze for achieving good reproducibility.

Means for Solving the Problem

To attain the above object, a heating apparatus for a gas chromatograph according to the present invention, in which a sample housed in a sample tube is heated for producing a vapor phase component that is transported by carrier gas from the sample tube to a detector, is characterized in that it comprises a temperature-elevating heating section for heating the sample tube and an instantaneous heating section for heating and pyrolyzing the sample by heating a ferromagnetic material around the sample to a Curie point.

The heating apparatus for a gas chromatograph of the present invention is characterized in that the temperature-elevating heating section is spaced away around a periphery of the sample tube, and the instantaneous heating section is spaced away around a periphery of the temperature-elevating heating section.

The heating apparatus for a gas chromatograph of the present invention is characterized in that it has an adsorption tube for collecting the vapor phase component split out from the sample tube.

The heating apparatus for a gas chromatograph of the present invention is characterized in that it comprises a first heating means that incrementally elevates the temperature of the sample heated by the temperature-elevating heating section, a second heating means that instantaneously heats the ferromagnetic material to the Curie point by the instantaneous heating section and also heats and pyrolyzes the sample, and a third heating means that heats the sample by the instantaneous heating section in the course of heating by the temperature-elevating heating section.

The heating apparatus for a gas chromatograph of the present invention, in which the sample in the sample tube is heated to produce a vapor phase component and such vapor phase component is fed by carrier gas from the sample tube towards a detector, is characterized in that a valve is capable of switching between a first state in which a first port and an eighth port are communicated, a second port and a third port are communicated, a fourth port and a fifth port are communicated, and a sixth port and a seventh port are communicated, and a second state in which the first port and the second port are communicated, the third port and the fourth port are communicated, the fifth port and the sixth port are communicated, and the seventh port and the eighth port are communicated, a communicating passage is provide between the second port and the sixth port, and a column is provided between the fourth port and the eighth port, in the first state, the vapor phase component that flows into the first port flows via the eighth port through the column and into the fourth port, and is fed to the detector via the fifth port, and purge gas supplied from the third port flows via the second port through the communicating passage to the sixth port, and is discharged from the seventh port, and in the second state, the vapor phase component that flows into the first port flows via the second port through the communicating passage to the sixth port, and is fed to the detector via the fifth port, and purge gas supplied from the third port flows via the fourth port through the column and flows into the eighth port, and is discharged from the seventh port.

A method for supplying heating for a gas chromatograph of the present invention using the above heating apparatus for a gas chromatograph is characterized in that it comprises the steps of heating the sample by the temperature-elevating heating section to elevate the temperature of sample, heating a ferromagnetic material around the elevated-temperature sample to the Curie point by the instantaneous heating section, and heating the sample whose temperature has been elevated, thereby pyrolyzing the sample.

Effect of the Invention

The heating apparatus for a gas chromatograph according to the present invention has the configuration described in the foregoing. In accordance with this configuration, the temperature-elevating heating section incrementally elevates the temperature of the sample to produce vapor phase components from volatile components of the sample. On the other hand the ferromagnetic material heated by the instantaneous heating section reaches the Curie point and becomes at a set temperature, and then the warped sample is instantly heated to be pyrolyzed. Namely, a non-volatile high molecular sample is pyrolyzed to a volatile low molecular to produce vapor phase components. Thus, the vapor phase components of the sample can be analyzed at an arbitrary temperature by using the temperature-elevating heating section; on the other hand, using the instantaneous heating section to instantaneously heat and pyrolyze the sample at the Curie point makes it possible to carry out analysis with good reproducibility.

Furthermore, according to the above configuration, since the temperature-elevating and instantaneous heating section can be used in succession, the vapor phase components are produced from the volatile components of a sample that has been heated by the temperature-elevating heating section and, in that state, the sample is heated instantaneously by the instantaneous heating section at an arbitrary temperature to be pyrolyzed. Thus, this makes it possible, for example, to analyze a composition before and after desorption and condensation reactions of a high molecular component sample.

The heating apparatus for a gas chromatograph of the present invention has the temperature-elevating heating section spaced away around the periphery of the sample tube, and the instantaneous heating section spaced away around the periphery of the temperature-elevating heating section. With this configuration, the temperature-elevating heating section, that is at a lower temperature comparing with the instantaneous heating section, is positioned close to the sample tube. Therefore, the heat generated by the temperature-elevating heating section can readily be conducted to the sample. Also, the temperature-elevating heating section and the instantaneous heating section are efficiently air-cooled by the space between the sample tube and the temperature-elevating heating section, and the space between the temperature-elevating heating section and the instantaneous heating section.

The heating apparatus for a gas chromatograph according to the present invention has an adsorption tube to collect gas phase components split out from the sample tube. With this configuration a gas phase component at an arbitrary temperature can be collected in the adsorption tube. Therefore, this makes it possible to arbitrary extract only a vapor phase component even from among compounds having similar boiling points.

The heating apparatus for a gas chromatograph according to the present invention has a first, second and third heating means, thereby allowing the sample to be heated by the heating means appropriate to the application.

The heating apparatus for a gas chromatograph according to the present invention has an eight-way valve, so that purge gas always flows through a flow path not in use, thereby preventing the sample from remaining in the flow path.

The heating method for a gas chromatograph according to the present invention is realized by the above heating apparatus for a gas chromatograph. With this configuration, when the sample is heated by the temperature-elevating heating section, the vapor phase components are produced from the volatile components, and in that state, the instantaneous heating section is used to instantaneously heat and pyrolize the sample at an arbitrary temperature. Therefore, this makes it possible, for example, to analyze a composition before and after desorption and condensation reactions of a high polymer component sample.

MODES FOR CARRYING OUT THE INVENTION

Embodiments of the invention will now be described with reference to the drawings.

Figure 1:
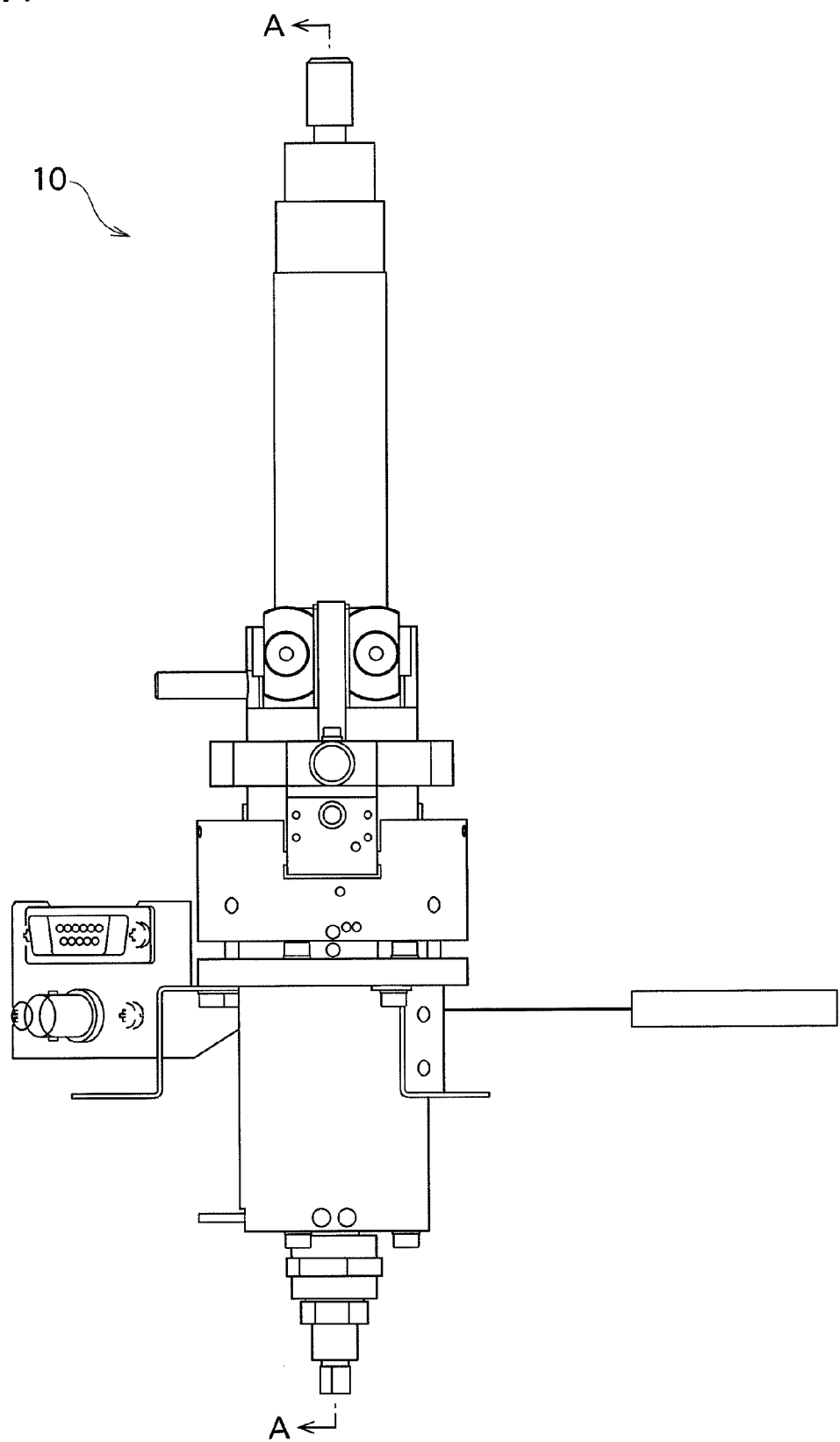
FIG. 1 is an external view of an embodiment of the heating apparatus for a gas chromatograph according to this invention.
Figure 2:
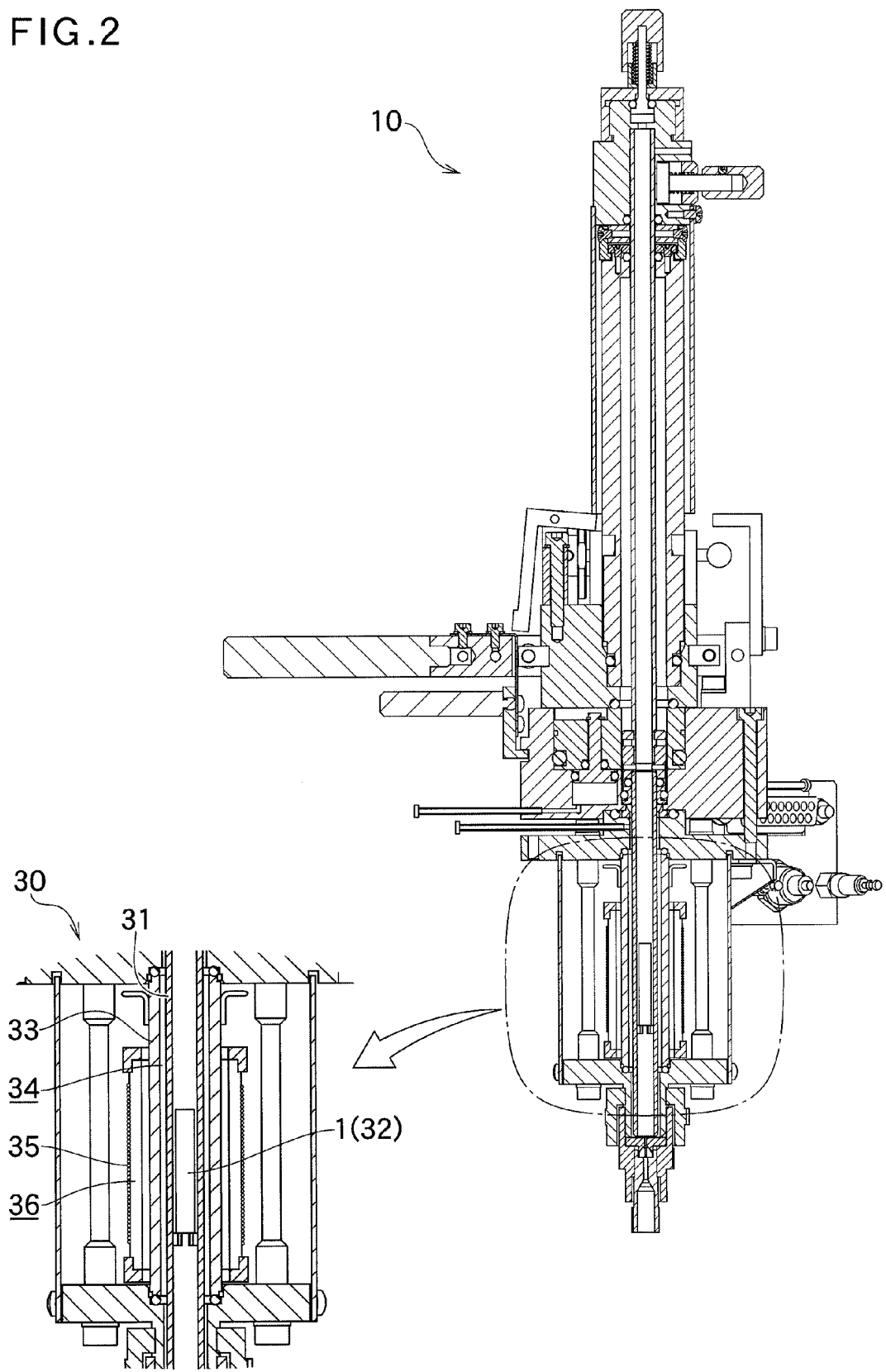
FIG. 2 is a sectional view along A-A of the embodiment of the heating apparatus for the gas chromatograph shown in FIG. 1, and an enlarged view of principal parts.

In FIGS. 1 and 2, a heating apparatus for a gas chromatograph 10 according to a present embodiment has a heating section 30, an eight-way valve 70 (see FIG. 3) for diverting the vapor phase components of sample 1, a detector (not shown) for detecting the vapor phase components that pass through the eight-way valve 70, a carrier gas supply section (not shown) that produces gas for carrying the vapor phase components to the detector, and so forth. The carrier gas is, for example, helium (He), argon (Ar) or nitrogen (N) or the like.

The heating section 30 is comprised of a sample tube 31 that contains the sample 1 whose composition is to be analyzed, a ceramic heater 33 that forms a temperature-elevating heating section disposed around the periphery of the sample tube 31, and a high-frequency coil 35 that forms an instantaneous heating section disposed around the periphery of the ceramic heater 33. A needle (not shown) is attached to the carrier gas downstream end of the sample tube 31. There is a space between the sample tube 31 and the ceramic heater 33, thereby forming a first void section 34. Similarly, there is a space between the ceramic heater 33 and the high-frequency coil 35, thereby forming a second void section 36.

The heating section 30 has a thermal insulation structure to prevent heat dissipation. The sample tube 31 is formed of a material such as heat-resistant glass, for example, that readily transmits the high-frequency waves of the high-frequency coil 35 and has low dielectric loss. The needle is formed of a corrosion-resistant material, e.g. stainless steel or the like. The ceramic heater 33 has a resistance thermometer whose maximum temperature is in the order of 1100 degrees. The high-frequency coil 35 is comprised, for example, of a bobbin made of ceramic having low dielectric loss and high thermal conductivity, around which wire, such as silver wire having high conductivity is wound, and is able to withstand a temperature in the order of 1100 degrees. The temperature elevation program is controlled by a controller (not shown).

The sample 1 is, for example, a low molecular material containing volatile components that become the vapor phase components when heated, a non-volatile high molecular material that becomes a low polymer material when pyrolized, a gas or the like. A pyrofoil 32 that forms a ferromagnetic material in which the sample 1 is wrapped is, for example, iron (Fe), nickel (Ni) or the like, and is subject to dielectric heating by the high-frequency coil 35. The pyrofoil 32 is selected according to a Curie point.

Figure 3A:
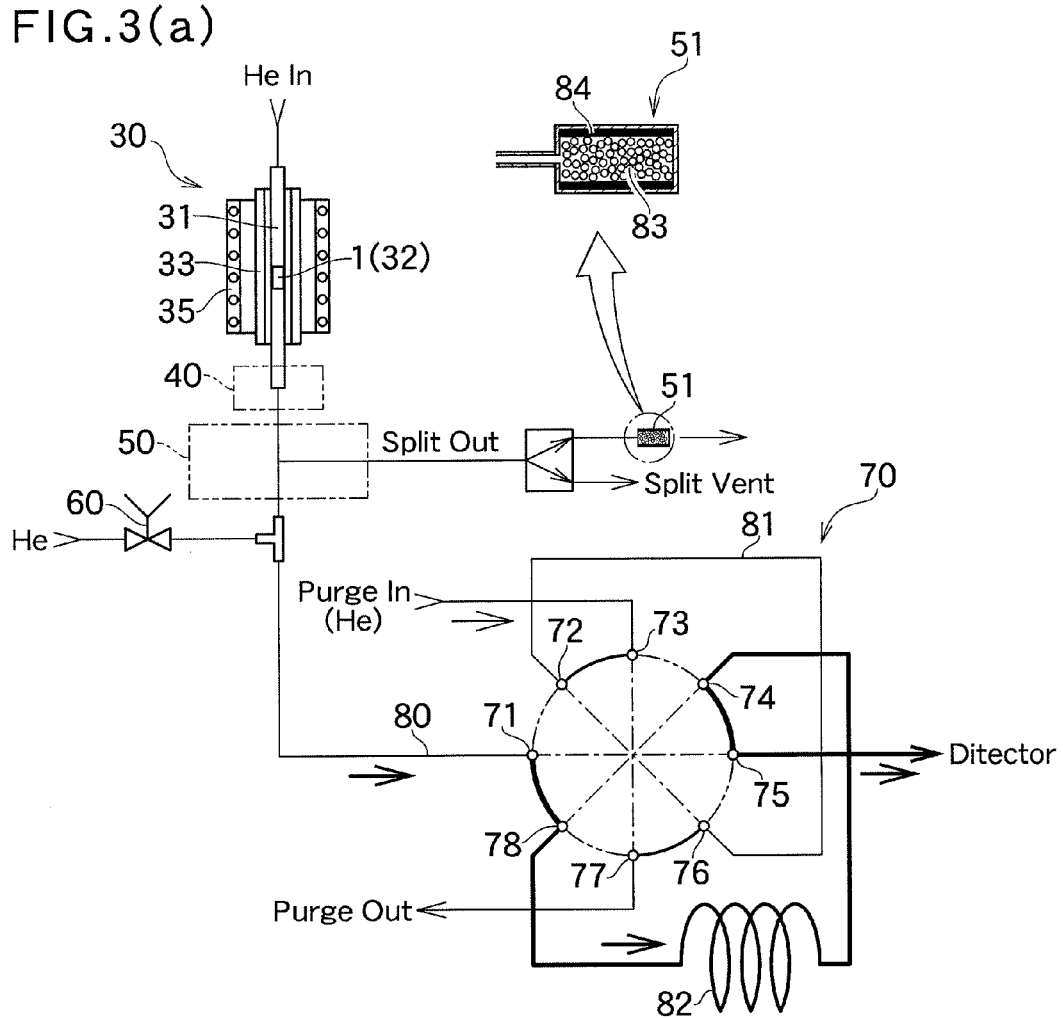
FIG. 3 is a flow path diagram showing the flow paths in the embodiment of the heating apparatus, with (a) showing the flow paths in a first state and (b) showing the flow paths in a second state.
Figure 3B:
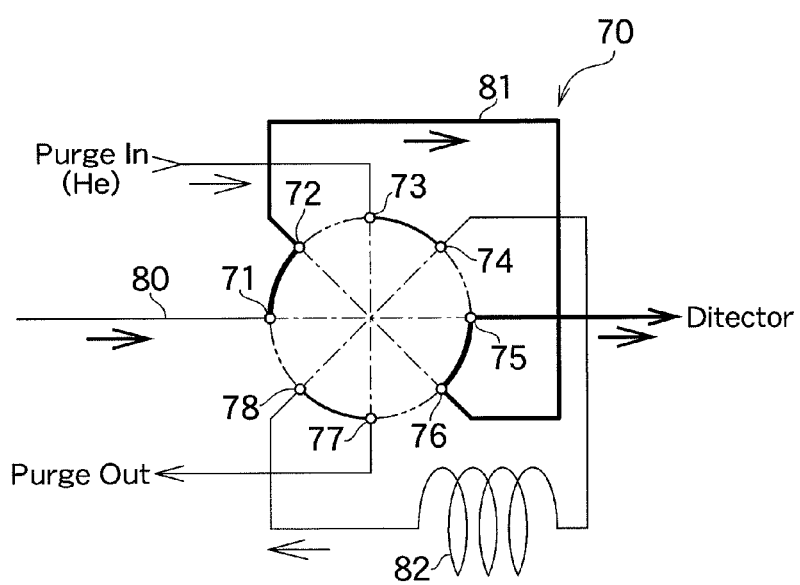

With reference to FIG. 3, there is a thermal insulation section 40 on the downstream end of the heating section 30, and further downstream, a splitter 50, a heart-cut valve 60, an eight-way valve 70, and a capillary column 82 are connected. The maximum temperature of the thermal insulation section is in the order of 400 degrees. The splitter 50 is used for the split mode or heart-cut, and the vapor phase components of the sample 1 are split out according to the application.

The split vapor phase components are collected in an adsorption tube 51 that is used for a primary trap. The adsorption tube 51 is formed of an adsorbent 83 wrapped in a ferromagnetic material 84. A liquid nitrogen cooling mechanism (not shown) may be attached to trap the vapor phase components at an entrance of the capillary column.

The eight-way valve 70 has eight valve ports and can be switched between a first state and a second state. With reference to FIG. 3 (a), in the first state, a first port 71 and eighth port 78 are communicated, second port 72 and third port 73 are communicated, fourth port 74 and fifth port 75 are communicated, and sixth port 76 and seventh port 77 are communicated. On the other hand, with reference to FIG. 3 (b), in the second state, the first port 71 and second port 72 are communicated, the third port 73 and fourth port 74 are communicated, the fifth port 75 and sixth port 76 are communicated, and the seventh port 77 and eighth port 78 are communicated.

A tube 80 is connected between the first port and the heating section 30, thereby forming a flow path therebetween through which the vapor phase components of the sample 1 are fed. An inert tube 81 is connected between the second port 72 and sixth port 76, thereby forming a connecting flow path therebetween. A capillary column 82 is connected between the fourth port 74 and eighth port 78. The third port 73 is on the purge gas supply side; the seventh port 77 is on the purge gas discharge side. The fifth port 75 is on the side for transportation to the detector. The purge gas is for example helium (He) or the like.

The first state shown in FIG. 3 (a) comprises a vapor phase component flow path that is a separation flow path (the bold line in the drawing), and a first purge flow path that is a purge gas flow path. Namely, the separation flow path route is the first port 71, eighth port 78, capillary column 82, fourth port 74 and fifth port 75, while the first purge flow path route is the third port 73, second port 72, inert tube 81, sixth port 76 and seventh port 77.

The second state of FIG. 3 (b) comprises a direct flow path serving as the gas phase component flow path (the bold line in the drawing), and a second purge flow path serving as the purge gas flow path. Namely, a direct flow path route is the first port 71, second port 72, inert tube 81, sixth port 76 and fifth port 75, while a second purge flow path is the third port 73, fourth port 74, capillary column 82, eighth port 78 and seventh port 77.

The heating apparatus for a gas chromatograph 10 has the above-described configuration.

Next, the operation of the heating apparatus for a gas chromatograph 10 will be described. The heating apparatus for a gas chromatograph 10 has three means of heating the sample 1. That is a heating by the ceramic heater 33 serving as a first heating means, a heating by the high-frequency coil 35 serving as a second heating means, and a heating by a third heating means by successive use of the first and second means.

The first heating means is a resistance heating system by the ceramic heater 33 wherein the temperature of the heated sample 1 is elevated incrementally. The sample 1 is housed in the sample tube 31 that has been heated to a prescribed temperature and then is heated by the ceramic heater 33. The per time rate of the temperature elevation is arbitrary. The sample 1 is heated incrementally, thereby producing the vapor phase components from the volatile components.

The second heating means is the Curie point heating system by the high-frequency coil 35, which instantaneously heats and pyrolyzes the sample 1. The sample 1 wrapped in the pyrofoil 32 is housed in the sample tube 31 and is heated by the high-frequency coil 35. When the pyrofoil 32 reaches the Curie point the temperature stays fixed, and the wrapped sample 1 is instantaneously heated and pyrolized. With the sample 1 thus pyrolized to a low molecular, the vapor phase components from each of the volatile components are produced.

With the third heating means, the sample 1 is heated by the high-frequency coil 35 in the course of heating the sample 1 by the ceramic heater 33. The temperature of sample 1 is elevated by the ceramic heater 33 and the pyrofoil 32 is heated by the high-frequency coil 35 at the temperature at which an arbitrary temperature state for producing the vapor phase components from the volatile components. When the pyrofoil 32 reaches the Curie point and the temperature becomes fixed, the sample 1 is instantaneously heated and pyrolized.

In FIG. 3, the vapor phase components produced from the sample 1 heated by any of the above heating means are transported, along with the carrier gas, from the needle through the tube 80 into the eight-way valve 70. The eight-way valve 70 is constantly supplied with the purge gas and has different vapor phase components and different purge gas flow paths depending on the first and second states.

In the first state of FIG. 3 (a), the vapor phase components flow along the separation flow path. Namely, the gas phase components flow in through the first port 71 and flow from the eighth port 78 into the capillary column 82, thereby being separated into each component. Each of thus separated vapor phase component flows into the fourth port 74 and is fed to the detector from the fifth port 75.

In the first state, the purge gas flows along the first purge gas flow path. Namely, the purge gas supplied via the third port 73 flows through the second port 72 into the inert tube 81, flows into the sixth port 76, and is discharged from the seventh port 77.

In the second state of FIG. 3 (b), the vapor phase components flow along the direct flow path. Namely, the gas phase components flow into the first port 71, flow from the second port 72 into the inert tube 81, flow into the sixth port 76, and is fed to the detector from the fifth port 75.

In the second state, the purge gas flows along the second purge gas flow path. Namely, the purge gas supplied via the third port 73 flows via the fourth port 74 into the capillary column 82, flows into the eighth port 78, and is discharged from the seventh port 77.

Depending on the aim of the analysis, the vapor phase components fed to the detector automatically undergo thermal decomposition analysis, generated gas analysis (thermobalance analysis method), fine structural analysis before and after desorption and condensation reactions, and so forth.

Further in FIG. 3, when the heart cut is used for the vapor phase component flow, the vapor phase components are collected by the adsorption tube 51 without passing through the eight-way valve 70. In this case, the adsorption tube 51 in which the vapor phase components are collected is housed in the sample tube 31 and heated by the second heating means (high-frequency coil 35). When the ferromagnetic material 84 reaches the Curie point the temperature stays fixed, and the vapor phase components adsorbed on the adsorbent 83 are thermally desorbed. The vapor phase components are transported to the eight-way valve 70 and passed through the capillary column 82, thereby being separated into each component.

Described next is the effect of the heating apparatus for a gas chromatograph 10 according to this embodiment.

According to the above-described embodiment, the heating section 30 comprises a sample tube 31 that houses the sample 1 whose composition is to be analyzed, the ceramic heater 33 disposed around the periphery of the sample tube 31, and the high-frequency coil 35 disposed around the periphery of the ceramic heater 33. With this configuration, the sample 1 is heated by any of the three means.

Namely, in the first heating means, the sample 1 is housed in the sample tube 31 that has been elevated to a prescribed temperature, and is heated by the ceramic heater 33. The sample 1 is incrementally heated, thereby producing the vapor phase components from the volatile components. Therefore, using the ceramic heater 33 the vapor phase components of the sample 1 can be analyzed (thermobalance analysis method) at an arbitrary temperature.

According to the second heating means, the sample 1 wrapped in the pyrofoil 32 is housed in the sample tube 31 and is heated by the high-frequency coil 35. When the pyrofoil 32 reaches the Curie point and the temperature stays fixed, the wrapped sample 1 is instantaneously heated and pyrolized in the order of 0.2 seconds, for example. With the sample 1 thus pyrolized to a low molecular, the vapor phase components from each of the volatile components are produced. Namely, even if the sample 1 is a non-volatile high molecular material, the vapor phase components are produced by heat pyrolysis of the volatile low molecular. Thus, using the high-frequency coil 35 to instantaneously heat and pyrolyze the sample 1 at the Curie point makes it possible to carry out analysis with good reproducibility.

According to the third heating means, the temperature of the sample 1 is elevated by the ceramic heater 33 and the pyrofoil 32 is heated by the high-frequency coil 35 at an arbitrary temperature state at which the vapor phase components are produced from the volatile components. When the pyrofoil 32 reaches the Curie point and the temperature becomes fixed, the sample 1 is instantaneously heated and pyrolized. Thus, this makes it possible to analyze a composition of, for example, plastic before and after desorption and condensation reactions, thereby enabling fine structural analysis of the plastic to be accomplished.

According to this embodiment, the split vapor phase components are collected in the adsorption tube 51 consisting of the adsorbent 83 wrapped in the ferromagnetic material 84. With this arrangement, the vapor components produced by the heating of the first heating means (by the ceramic heater 33) is collected by the absorption tube 51 as arbitrary vapor phase components split out by heart-cut. By housing the adsorption tube 51 in the sample tube 31, thermal desorption can be carried out by heating of the second heating means (high-frequency coil 35), and the vapor phase components are separated by passing through the capillary column 82. Thus, this can provide accurate detector measurement of compounds having similar boiling points, such as isomers. Namely, drawbacks of generated gas analysis (EGA method) can be resolved.

For reference, the drawbacks of the EGA method are as follows. Namely, according to the EGA method, the vapor phase components produced by heating of the first heating means are transported to the detector via the inert tube 81 having no separation capability. For this reason, compounds such as isomers having similar boiling points are produced at the same time and detected as a mixture.

According to this embodiment, there is the space between the sample tube 31 and the ceramic heater 33 to from the first void section 34. Similarly, there is a space between ceramic heater 33 and the high-frequency coil 35 to form the second void section 36. With this configuration, the ceramic heater 33 whose temperature is lower compared with the high-frequency coil 35 is positioned close to the sample tube 31. Thus, the heat generated by the ceramic heater 33 can readily be conducted to the sample 1. Also, the ceramic heater 33 and the high-frequency coil 35 are air-cooled and effectively cooled by the first void section 34 and the second void section 36.

According to this embodiment, the first purge flow path route with the eight-way valve 70 in the first state is the third port 73, second port 72, inert tube 81, sixth port 76 and seventh port 77. On the other hand, the second purge flow path route in the second state is the third port 73, fourth port 74, capillary column 82, eighth port 78 and seventh port 77. With this configuration in the first state, the purge gas supplied via the third port 73 flows through the second port 72 into the inert tube 81, flows into the sixth port 76, and is discharged from the seventh port 77. On the other hand, in the second state, purge gas supplied via the third port 73 flows via the fourth port 74 into the capillary column 82, flows into the eighth port 78, and is discharged from the seventh port 77. Namely, in both the first and second states, the purge gas always flows through the flow path that is not in use. This prevents the sample 1 from remaining in the flow path.

According to this embodiment, the separation flow path route of the eight-way valve 70 in the first state (the bold line in FIG. 3 (*a*)) is the first port 71, eighth port 78, capillary column 82, fourth port 74 and fifth port 75. With this configuration, in the first state, the vapor phase components that flow into the first port 71 flow from the eighth port 78 into the capillary column 82, thereby being separated into each component. Each of thus separated vapor phase component flows into the fourth port 74, and is fed to the detector from the fifth port 75.

On the other hand, the direct flow path route in the second state (the bold line in FIG. 3 (*b*)), is the first port 71, second port 72, inert tube 81, sixth port 76 and fifth port 75. With this configuration, in the second state the vapor phase components flow into the first port 71, flow out of the second port 72 into the inert tube 81, flow into the sixth port 76, and is fed to the detector from the fifth port 75.

Thus, when separated vapor phase components of the sample 1 are fed to the detector, the sample 1 can be passed through the capillary column 82 by selecting the first state, while when the EGA method is used for real-time monitoring of the vapor phase components, the sample 1 can be fed to the detector via the inert tube 81 by selecting the second state.

While the embodiment of the invention has been described in the foregoing, the invention is not limited to the described embodiment, and various design modifications can be made to the extent that does not depart from the scope of the invention as defined in the scope of the patent claims. For example, the following can be considered as having possible industrial applicability. Namely, in the field of food packaging, the development of packaging materials that suppress the smell of plastic or smells arising when heating by a microwave oven is used, and research related to extending a shelf life; the development of functional packaging material; in the field of engineering plastics, research leading to the development of viscoelastic materials that are heat resistant and wear resistant; in the rubber industry, preventing tires bursting and developing eco-tires by improving tackifier ratings based on ratings of rubber and plastic properties; in the analysis of high molecular additives, analysis of high molecular additive composition by thermobalance analysis method; and in the criminal investigation field, expert opinion in properties ratings based on generated gas analysis or thermobalance analysis method and the like.

DESCRIPTION OF SYMBOLS

1 Sample
10 Heating apparatus for a gas chromatograph
20 Carrier gas supply section
30 Heating section
31 Sample tube
32 Pyrofoil (ferromagnetic material)
33 Ceramic heater (temperature-elevating heating section)
34 First void section
35 High-frequency coil (instantaneous heating section)
36 Second void section
40 Thermal insulation section
50 Splitter
51 Adsorption tube
60 Heart-cut valve
70 Eight-way valve
71 First port
72 Second port
73 Third port
74 Fourth port
75 Fifth port
76 Sixth port
77 Seventh port
78 Eighth port
80 Tube (inflow path)
81 Inert tube (connecting flow path)
82 Capillary column
83 Adsorbent
84 Ferromagnetic material

The invention claimed is:

1. A heating apparatus for a gas chromatograph having a sample housed in a sample tube is heated for producing a vapor phase component, the vapor phase component being transported by a carrier gas from the sample tube to a detector, comprising:
a temperature-elevating heating section for heating the sample; and
an instantaneous heating section for heating and pyrolyzing the sample by heating a ferromagnetic material around the sample to a Curie point;
the heating apparatus further comprising:
a valve capable of switching between a first state in which a first port and an eighth port are communicated, a second port and a third port are communicated, a fourth port and a fifth port are communicated, and a sixth port and a seventh port are communicated, and a second state in which the first port and the second port are communicated, the third port and the fourth port are communicated, the fifth port and the sixth port are communicated, and the seventh port and the eighth port are communicated,
a communicating passage between the second port and the sixth port, and
a column between the fourth port and the eighth port;
wherein in the first state, the vapor phase component that flows into the first port flows via the eighth port through the column and into the fourth port, and is fed to the detector via the fifth port, and a purge gas supplied from the third port flows via the second port through the communicating passage to the sixth port, and is discharged from the seventh port, and
in the second state, the vapor phase component that flows into the first port flows via the second port through the communicating passage to the sixth port, and is fed to the detector via the fifth port, and the purge gas supplied from the third port flows via the fourth port through the column and flows into the eighth port, and is discharged from the seventh port.

2. The heating apparatus for a gas chromatograph according to claim 1, wherein the temperature-elevating heating section is spaced away around a periphery of the sample tube, and the instantaneous heating section is spaced away around a periphery of the temperature-elevating heating section.

3. The heating apparatus for a gas chromatograph according to claim 2, further comprising an adsorption tube for collecting a vapor phase component split out from the sample tube.

4. A heating method for a gas chromatograph that uses the heating apparatus for a gas chromatograph according to claim 3, comprising the steps of heating the sample by the temperature-elevating heating section to elevate a temperature of the sample, heating the ferromagnetic material around the elevated-temperature sample to the Curie point by the instantaneous heating section, and heating the sample whose temperature has been elevated to pyrolyze the elevated-temperature sample.

5. A heating method for a gas chromatograph that uses the heating apparatus for a gas chromatograph according to claim 2, comprising the steps of heating the sample by the temperature-elevating heating section to elevate a temperature of the sample, heating the ferromagnetic material around the elevated-temperature sample to the Curie point by the instantaneous heating section, and heating the sample whose temperature has been elevated to pyrolyze the elevated-temperature sample.

6. The heating apparatus for a gas chromatograph according to claim 1, further comprising an adsorption tube for collecting a vapor phase component split out from the sample tube.

7. A heating method for a gas chromatograph that uses the heating apparatus for a gas chromatograph according to claim 6, comprising the steps of heating the sample by the temperature-elevating heating section to elevate a temperature of the sample, heating the ferromagnetic material around the elevated-temperature sample to the Curie point by the instantaneous heating section, and heating the sample whose temperature has been elevated to pyrolyze the elevated-temperature sample.

8. A heating method for a gas chromatograph that uses the heating apparatus for a gas chromatograph according to claim 1, comprising the steps of heating the sample by the temperature-elevating heating section to elevate a temperature of the sample, heating the ferromagnetic material around the elevated-temperature sample to the Curie point by the instantaneous heating section, and heating the sample whose temperature has been elevated to pyrolyze the elevated-temperature sample.

\* \* \* \* \*